United States Patent [19]

Mayr et al.

[11] 3,960,541
[45] June 1, 1976

[54] PROCESS FOR REGULATING OR INFLUENCING THE GROWTH AND METABOLISM OF PLANTS

[75] Inventors: Hubert Mayr, Leonding near Linz; Elfriede Presoly; Ferdinand Weinrotter, both of Linz; Walter Müller, Leonding near Linz; Gerhard Stern, Linz, all of Austria; Walter Mizzi, deceased, late of Pasching near Linz, Austria, by Maria Frohner

[73] Assignee: Chemie Linz Aktiengesellschaft, Austria

[22] Filed: Jan. 3, 1975

[21] Appl. No.: 539,434

Related U.S. Application Data

[62] Division of Ser. No. 232,973, March 8, 1972, Pat. No. 3,877,923.

[30] Foreign Application Priority Data

Mar. 8, 1971    Austria .............................. 2000/71

[52] U.S. Cl. .................................................... 71/88
[51] Int. Cl.$^2$ .......................................... A01N 9/28
[58] Field of Search .............................. 71/88, 113

[56] References Cited
UNITED STATES PATENTS
3,117,856    1/1964    Darlington ............................ 71/106

OTHER PUBLICATIONS
Oertli, Chem. Abst., vol. 59 (1963).
Kuiper, Chem. Abst., vol. 76, (1972).

Primary Examiner—Lewis Gotts
Assistant Examiner—Catherine L. Mills
Attorney, Agent, or Firm—Wenderoth, Lind & Ponack

[57] ABSTRACT

The resistance of plants to environmental factors such as drought is increased by treating the plants themselves, their seeds before sowing or the surrounding soil, before or after emergence of the plants, with compositions containing aliphatic epoxymonocarboxylic acids containing one to three epoxy groups and 6 to 22 carbon atoms or the salts, lower alkyl esters, lower polyhydroxyalkyl esters, amides, monoalkylamides and dialkylamides thereof as active ingredient.

10 Claims, No Drawings

PROCESS FOR REGULATING OR INFLUENCING THE GROWTH AND METABOLISM OF PLANTS

This is a division of application Ser. No. 232,973, filed Mar. 8, 1972, now U.S. Pat. No. 3,877,923.

This invention relates to a process for regulating or influencing the growth and metabolism of plants in order to increase their resistance to environmental factors such as drought.

Substances which influence the growth of plants without being nutrients have been known for some time. These include, for example, weedkillers possessing a hormone action, such as 2,4-dichlorophenoxyacetic acid, or so-called growth regulators such as chlorocholine chloride, which in wheat causes the formation of shorter and stronger stalks. Furthermore, decenylsuccinic acid is a substance which imparts higher drought resistance and frost resistance to the crop plants treated therewith. In the copending application Ser. No. 834,170 of Walter Muller et al, of June 17, 1969 the influence of $\alpha$-substituted aliphatic carboxylic acids on the growth of plants is disclosed It has now been found that epoxy derivatives of unsaturated fatty acids are capable of influencing the growth and metabolism of plants, especially their water balance, so that plants treated therewith exhibit increases in yield and increased resistance to environmental factors, such as, for example, drought. The reasons for these effects may reside on the one hand in a reduced water throughput of the plants through reduction of transpiration and on the other hand in an increased ability of the plants treated with the substance to absorb water.

Accordingly the present invention provides a process for influencing the growth and metabolism of plants, especially for influencing their water balance, which comprises treating the plants themselves, their seeds before sowing or the surrounding soil before or after emergence of the plants, which at least one aliphatic epoxymonocarboxylic acid containing one or more epoxy groups and 6 to 22 carbon atoms, or a salt, lower alkyl ester, lower polyhydroxyalkyl ester such as triglycerides, amide monoalkylamide or dialkylamide thereof.

Particularly preferred epoxymonocarboxylic acids are those derived from naturally occurring unsaturated fatty acids, such as, for example, oleic acid, linoleic acid, linolenic acid, palmitoleic acid or erucic acid. These may be converted into mono-, bis- or tris-epoxyacids by means of conventional epoxidation processes, for example with the aid of per-acetic acid. In the same way, other unsaturated monocarboxylic acids, for example the octenoic acids, the decenoic acids and the undecenoic acids, also may be epoxidised.

Accordingly the present invention also provides a process for the preparation of a composition as described above which comprises epoxidising a naturally occurring mixture of esters of unsaturated fatty acids or the isolated, and optionally chemically modified, constituents thereof and mixing the resulting active ingredient with one or more liquid or solid extenders or diluents.

As examples of epoxy-acids prepared in accordance with the process there may be mentioned: 4,5-epoxyoctanoic acid, 5,6-epoxydecanoic acid, 10,11-epoxyundecanoic acid, 9,10-epoxyhexadecanoic acid, 9,10-epoxystearic acid, 9,10-12,13-diepoxystearic acid and 9,10-12,13-15,15-triepoxystearic acid; 9,10-epoxystearic acid deserving to be singled out particularly.

Instead of the pure acids, it is also possible to use mixtures of epoxy-acids or mixtures of triglycerides of these epoxy-acids which are obtained by epoxidation of naturally occurring oils before or after their saponification. Here again the epoxidation is carried out in accordance with methods which are in themselves known. Such oils are, for example, olive oil, which normally contains about 82% of oleic acid and 6% of linoleic acid, in addition to 9% of palmitic acid; groundnut oil, which normally contains about 56% of oleic acid and 26% of linoleic acid; soya bean oil containing about 50% of linoleic acid, 30% of oleic acid and 2% of linolenic acid in addition to palmitic acid and stearic acid; linseed oil containing about 45% of linolenic acid, 24% of linoleic acid and 20% of oleic acid in addition to palmitic acid and stearic acid; and rape oil containing about 50% of erucic acid in addition to 16% of oleic acid, 12% of linoleic acid and 10% of linolenic acid as well as stearic acid and palmitic acid. The use of such epoxidised oils or of the epoxy derivatives of the fatty acid mixtures manufactured therefrom is attractive especially for economic reasons. The epoxidation may be carried out before or after saponification of the oils. A further modification of the carboxyl group by converting the esters or acid groups into salts, amides or esters of other alcohols or converting the esters into acids is also possible after the epoxidation.

The compositions according to the invention may be administered either in the liquid form or in the solid form, an both absorption of the agents via the plant and via the soil is successful. The compositions may be used not only after emergence of the plants but also equally well before emergence of the plants, by introduction into the soil. When used in the liquid form, which is preferentially possible in the form of an aqueous spray, the active substances are either emulsified or dissolved, depending on their solubility, and in the former case the use of an emulsifier, for example a mixture of an alkylarylsulphonate with polyoxyethylene-sorbitan, is advisable. In some cases, above all if the agents are to be administered via the leaves, the addition of a wetting agent, for example, an alkylphenyl-polyethylene-ether, proves advantageous since the leaves are then wetted better. Emulsifiers, such as, for example sodium oleylmethyltauride, also may be added to the composition in solid form, whilst any customary solid extender, such as, for example, certain finely ground types of clay, are suitable as an inert carrier for the solid form. Finally, the compositions according to the invention also may be applied as a dressing to seeds before sowing. The amount used may vary considerably and is adapted to the prevailing conditions. As a rule it is between 0.5 and 15 kg/ha. relative to the free acid.

In all types of use the active substances may be present either as the free acid or as a salt, ester or amide thereof. Salts which may be mentioned, apart from the alkali metal salts and ammonium salts, are above all salts with organic bases, such as trimethylamine, diethanolamine and triethanolamine. Possible esters, in addition to those with lower aliphatic alcohols, such as methyl esters, ethyl esters and butyl esters, are those with polyhydric alcohols. Amides which may be used include those which carry one or two lower alkyl radicals on the amide nitrogen.

The compositions according to the invention may be used not only by themselves but also in admixture with other substances, such as inorganic or organic fertilisers, plant protection agents, growth regulators and/or soil improvement agents.

The compositions according to the invention and their action on plants are illustrated in more detail in the Examples which follow. The parts quoted therein are parts by weight.

EXAMPLE 1

Mixing of 20 parts of 9,10-epoxystearic acid, 70 parts of kaolin and 10 parts of sodium oleylmethyltauride (33% strength) yields a solid mixture which may be suspended in water. The suspension may be used as a spraying agent.

The 9,10-epoxystearic acid is obtained by epoxidation of oleic acid with peracetic acid.

EXAMPLE 2

30 parts of 9,10-epoxystearic acid, 10 parts of a mixture of an alkylarylsulphonate with a polyoxymethylenealkylphenol, 15 parts of dimethylformamide and 45 parts of xylene yield a liquid mixture which may be emulsified in water and used as a spraying agent.

EXAMPLE 3

10 parts of the sodium salt of 9,10-epoxystearic acid and 0.25 part of ethyl-polyglycol-ether as a wetting agent are dissolved in 88.7 parts of water with the addition of one part of ethylenediaminetetraacetic acid. This solution serves as the basis for a spraying agent and may be brought to the desired concentration, immediately prior to use, by dilution with water.

EXAMPLE 4

40 parts of a mixture of epoxidised fatty acid esters obtained by epoxidising a soya bean oil of composition 33.5% of oleic acid, 52.5% linoleic acid, 2.3% linolenic acid, 6.5% palmitic acid and 4.5% stearic acid and containing 15.9% of epoxy groups, was mixed with 10 parts of a mixture of alkylarylsulphonate and polyoxyethylene triglyceride and 50 parts of xylene. The liquid mixture thereby obtained may be emulsified in water and used as a spraying agent.

The epoxidation of the soya bean oil was carried out by means of peracetic acid.

EXAMPLE 5

In a similar manner, a concentrate, which may be emulsified in water and used as a spraying agent, may be prepared from 20 parts of the mixture of epoxidised fatty acid esters described in Example 4, 70 parts of xylene and 10 parts of polyethylene-sorbitan-tall oil ester.

9-10,12-13-Diepoxystearic acid, 9-10,12-13,15-16-triepoxystearic acid, 3,4-epoxyoctanoic acid and 10,11-epoxyundecanoic acid as well as their salts, esters and amides may be formulated analogously as spraying powders or as emulsion concentrates. The fatty acid mixtures obtained by saponification of naturally occurring oils, as well as the epoxidised oils, such as rape oil and linseed oil themselves, also may be converted into spraying agents in the same manner.

The Examples which follow are intended to illustrate the action of the compositions according to the invention. The acids tested therein were formulated according to Example 1, and the epoxidised soya bean oil was formulated according to Example 5.

EXAMPLE 6

Marrowstem cabbage was grown in Mitscherlich pots. After emergence, the plants were thinned out to 3 per pot. When they had grown to 20 cm, they were treated using an amount of 5 kg/ha of the active substance mentioned below. The treatment was carried out as a leaf spray, using an amount of water of 400 l/ha. In order to achieve better wetting, an alkylphenol-polyethylene-ether was added as the wetting agent. After treatment, the pots were supplied with varying amounts of water, namely at 40%, 60% and 80% water capacity. After a period of growth of about 16 weeks, the pots were harvested. This gave the following harvest yield:

|  | Fresh weight g/pot | | |
|---|---|---|---|
|  | 40% | 60% | 80% |
|  | Water capacity | | |
| 9,10-Epoxystearic acid, 5 kg/ha | 283.6 | 328.4 | 318.3 |
| Control | 260.1 | 298.2 | 292.4 |

EXAMPLE 7

The following experiment was carried out in order to ascertain the effect on the transpiration of the plants:

4 seeds of Vicia faba were placed in plastic pots which were filled with Rettenbacher soil. After the seedlings had appeared, the plants were reduced to two per pot. After 10 to 11 days, when the plants had fully developed 2 pairs of leaves and had reached a height of 7 to 10 cm, they were treated by spraying with aqueous solutions of 9,10-epoxystearic acid and 10,11-epoxyundecanoic acid in concentrations of $10^0$, $10^{-1}$ and $10^{-2}\%$. One week after the treatment, when the plants had developed 3 to 4 pairs of leaves and were at a height of 19 to 24 cm, the water released by the plants was determined. In order to increase the accuracy, the experiment was carried out in a climatically controlled chamber. For each treated plant, an untreated control plant was measured at approximately the same time in this experiment, in order to take account of the variation in transpiration over the course of the day. As a measure of the transpiration, the relative transpiration in % was determined according to the formula $$\text{Relative transpiration} = \frac{\text{Surface transpiration, mg/dm}^2 \times \text{minutes}}{\text{Evaporation, mg/dm}^2 \times \text{minutes}} \times 100.$$

In this formula, the surface transpiration denotes the evaporation of water from the moist surfaces of the living plant tissues, whilst evaporation represents the vaporisation of water from moistened green filter paper discs (= Piche discs). The results are recorded in the table below.

| Concentration of 9,10-epoxystearic acid in the solution | Transpiration intensity mg/g of fresh weight min. | Evaporation mg/dm² min. | mg/dm² min. | Relative transpiration in % |
|---|---|---|---|---|
| $10^{-2}$ | 10.4 | 10.9 | 35.9 | 30.4 |
| Control | 18.3 | 18.0 | 35.9 | 50.8 |
| $10^{-1}\%$ | 4.2 | 4.2 | 33.6 | 12.5 |
| Control | 14.2 | 15.3 | 33.6 | 45.7 |
| $10^0\%$ | 9.4 | 8.7 | 36.2 | 24.2 |
| Control | 21.3 | 22.7 | 36.2 | 62.9 |
| $10^0\%$ | 4.0 | 3.8 | 35.4 | 10.8 |
| Control | 10.3 | 10.0 | 35.4 | 28.4 |

-continued

| Concentration of 9,10-epoxy-stearic acid in the solution | Transpiration intensity mg/g of fresh weight min. | Evaporation mg/dm² min. | mg/dm² min. | Relative transpiration in % |
|---|---|---|---|---|

| Concentration of 10,11-epoxy-undecanoic acid in the solution | Transpiration intensity mg/g of fresh weight min. | mg/dm² min. | Evaporation mg/dm² min. | Relative transpiration in % |
|---|---|---|---|---|
| $10^{-2}$ % | 5.6 | 6.3 | 37.4 | 17.4 |
| Control | 6.9 | 7.7 | 37.4 | 20.7 |
| $10^{-1}$ % | 6.2 | 7.1 | 38.6 | 18.8 |
| Control | 7.5 | 9.2 | 38.6 | 23.9 |
| $10^{0}$% | 8.0 | 8.9 | 41.2 | 21.8 |
| Control | 10.4 | 12.1 | 41.2 | 29.6 |

The varying transpiration rates are conditioned by the variation in transpiration of the plant over the course of a day.

The results show that 9,10-epoxystearic acid and 10,11-epoxyundecanoic acid have the effect of reducing the transpiration as compared to the controls.

EXAMPLE 8

The Example which follows presents the results of the experiment with 9,10-12,13-15,16-triepoxystearic acid. The experiments are carried in the same way as in Example 7.

| Concentration of triepoxy-stearic acid in the solution | Transpiration intensity mg/g of fresh weight min. | mg/dm² min. | Evaporation mg/dm² min. | Relative transpiration in % |
|---|---|---|---|---|
| $10^{-2}$ % | 12.2 | 12.3 | 34.6 | 35.8 |
| Control | 12.3 | 13.5 |  | 39.3 |
| $10^{-1}$ % | 8.9 | 9.7 | 31.3 | 31.1 |
| Control | 12.8 | 13.8 |  | 44.1 |
| $10^{0}$% | 12.4 | 13.6 | 32.7 | 41.8 |
| Control | 10.9 | 12.5 |  | 38.3 |
| $10^{0}$% | 11.9 | 12.9 | 34.8 | 37.2 |
| Control | 11.7 | 12.4 |  | 35.6 |

The results show that 9,10-12,13-15,16-triepoxystearic acid also reduces transpiration as compared to the controls.

EXAMPLE 9

As an example of a mixture of an epoxidised fatty acid ester, epoxidised soya bean oil was used in aqueous solutions at concentrations of $10^{0}$, $10^{-1}$ and $10^{-2}$%.

The soya bean oil acids had the following distribution:
33.5% of oleic acid
52.5% of linoleic acid
2.3% of linolenic acid
6.5% of palmitic acid and
4.5% of stearic acid.

The epoxidised soya bean oil contained 15.9% of epoxy groups ($C_2O$).

The experiment was again carried out as in Example 7.

The results are summarised in the table:

| Concentration of epoxidised soya bean oil in the solution | Transpiration intensity mg/g of fresh weight min. | mg/dm² min. | Evaporation mg/dm² min. | Relative transpiration in % |
|---|---|---|---|---|
| $10^{-2}$ % | 7.5 | 7.5 | 14.9 | 50.7 |
| Control | 8.3 | 8.1 |  | 54.9 |
| $10^{-1}$ % | 10.9 | 9.4 | 18.3 | 51.8 |
| Control | 12.4 | 11.5 |  | 62.9 |
| $10^{0}$% | 7.6 | 6.8 | 23.6 | 29.1 |
| Control | 9.0 | 8.7 |  | 36.9 |
| $10^{0}$% | 6.5 | 6.3 | 16.8 | 37.9 |
| Control | 8.5 | 7.5 |  | 44.8 |

Here again the transpiration-inhibiting action is shown clearly.

EXAMPLE 10

Chinese cabbage was grown in Mitscherlich pots. After emergence, the plants were thinned out to 3 per pot. 6 weeks after germination, the treatment with 3,4-epoxyoctanoic acid was carried out, using an amount corresponding to 2.5 kg/ha. The treatment was carried out as a leaf spray using an amount of water corresponding to 400 l/ha. In order to achieve beter wetting, an alkylphenol-polyethylene-ether was added as the wetting agent. After the treatment, the pots were kept at 40% water capacity. After a period of growth of about 10 weeks, the pots were harvested. The harvest yields are summarised in the table below:

|  | Fresh weight in g/pot |
|---|---|
| Control | 261.4 |
| 3,4-Epoxyoctanoic acid | 317.5 |

EXAMPLE 11

Marrowstem cabbage was grown in Mitscherlich pots. After emergence, the plants were thinned out to 3 per pot. When they had grown to a height of 40 cm, they were treated with 9,10-12,13-diepoxystearic acid using an amount corresponding to 2.5, 5 and 7.5 kg/ha. The treatment was carried out as a leaf spray using an amount of water of 400 l/ha. In order to achieve better wetting, an alkylphenol-polyethylene-ether was added as the wetting agent. After the treatment, the pots were kept at 40% water capacity. After a period of growth of 16 weeks the pots were harvested. Hereupon the following harvest yields were obtained:

|  | Dry weight in g/pot |
|---|---|
| Control | 98.8 |
| Diepoxystearic acid |  |
| 2.5 kg/ha | 103.5 |
| 5 kg/ha | 102.5 |
| 7.5 kg/ha | 112.8 |

EXAMPLE 12

Winter wheat was grown in Mitscherlich pots. After germination it was thinned out to 19 plants. At the beginning of the elongation of the stalk (Stage I) some of the plants were treated with 9,10-12,13-diepoxystearic acid whilst the remainder was only subjected to the treatment with 9,10-12,13-diepoxystearic acid at the time of coming into ear (Stage II). The amount used was in both cases 2.5 and 5 kg/ha. The treatment was carried out as a leaf spray using an amount of water corresponding to 400 l/ha. In order to achieve better wetting, an alkylphenol-polyethylene-ether was added as the wetting agent. After the treatment, the pots were kept at 80% water capacity. After the plants had ripened, the pots were harvested.

| Control | Weight of corn/ear (Fresh weight, g/pot) 71.92 | | | |
|---|---|---|---|---|
|  | Stage I | | Stage II | |
| Diepoxystearic acid | 2.5 kg/ha 80.05 | 5 kg/ha 75.02 | 2.5 kg/ha 83.77 | 5 kg/ha 83.12 |

EXAMPLE 13

As an example of a mixture of epoxidised fatty acids, epoxidised linseed oil fatty acids in aqueous solutions, at concentrations of $10^0$, $10^{-1}$ and $10^{-2}$ were used.

The linseed oil acids had the following distribution:
45% of linolenic acid
24% of linoleic acid
21% of oleic acid
5.6% of palmitic acid and
3.5% of stearic acid.

The linseed oil was saponified to give a corresponding mixture of unsaturated and saturated fatty acids and this mixture was oxidised by means of per-acetic acid. The epoxy group content was 19.8%.

The test of the transpiration-inhibiting action was carried out as described in Example 7.

The results are summarised in the table:

| Concentration of epoxidised linseed oil fatty acids in the solution | Transpiration intensity mg/g of fresh weight min. | mg/dm² min. | Evaporation mg/dm² min. | Relative transpiration in % |
|---|---|---|---|---|
| $10^{-2}$ % | 6.8 | 6.8 | 31.6 | 21.7 |
| Control | 7.4 | 7.7 | 31.6 | 24.6 |
| $10^{-1}$ % | 10.1 | 10.1 | 30.0 | 34.0 |
| Control | 13.3 | 13.9 | 30.0 | 46.4 |
| $10^0$ | 6.6 | 7.0 | 29.2 | 24.2 |
| Control | 16.5 | 18.2 | 29.2 | 62.3 |

The results show that epoxidised linseed oil fatty acids have the effect of reducing transpiration as compared to the controls.

What we claim is:

1. A process for increasing the resistance of plants to drought, which comprises treating their seeds before sowing with an active compound selected from the group consisting of aliphatic epoxymonocarboxylic acids containing one to three epoxy groups and 6 to 22 carbon atoms and the salts, lower alkyl esters, lower polyhydroxyalkyl ester, amides, monoalkylamides and dialkylamides thereof.

2. A process according to claim 1, in which the active ingredient is a mixture of triglycerides of the aliphatic epoxymonocarboxylic acids, which have been obtained by epoxidising a naturally occurring mixture of triglycerides of unsaturated fatty acids.

3. A process according to claim 1, in which the active ingredient is a mixture of the aliphatic epoxymonocarboxylic acids, which have been obtained by saponification of a naturally occurring mixture of triglycerides of unsaturated fatty acids and epoxidation of the resulting mixture of unsaturated fatty acids.

4. A process according to claim 1, in which the active ingredient is 9,10-epoxystearic acid.

5. A process for increasing the resistance of plants to drought, which comprises treating the surrounding soil, before or after emergence of the plants, with an active compound selected from the group consisting of aliphatic epoxymonocarboxylic acids containing one to three epoxy groups and 6 to 22 carbon atoms and the salts, lower alkyl esters, lower polyhydroxyalkyl ester, amides, monoalkylamides and dialkylamides thereof.

6. A process according to claim 5, in which the active compound is administered to the soil in an amount of 0.5 to 15 kg per hectare relative to the free acid.

7. A process according to claim 5, in which the treatment is carried out by watering or spraying the soil with an aqueous mixture which contains the active compound in a dissolved, suspended or emulsified form.

8. A process according to claim 5, in which the active ingredient is a mixture of triglycerides of the aliphatic epoxymonocarboxylic acids, which have been obtained by epoxidizing a naturally occurring mixture of triglycerides of unsaturated fatty acids.

9. A process according to claim 5, in which the active ingredient is a mixture of the aliphatic epoxymonocarboxylic acids, which have been obtained by saponification of a naturally occurring mixture of triglycerides of unsaturated fatty acids and epoxidation of the resulting mixture of unsaturated fatty acids.

10. A process according to claim 5, in which the active ingredient is 9,10-epoxystearic acid.

\* \* \* \* \*